US011433188B2

(12) United States Patent
Greiner-Perth (10) Patent No.: US 11,433,188 B2
(45) Date of Patent: Sep. 6, 2022

(54) INHALATION DEVICE FOR THE PURPOSE OF INHALATION OF A DROPLET MIST (71) Applicant: APTAR RADOLFZELL GMBH, Radolfzell (DE)

(72) Inventor: Jürgen Greiner-Perth, Gottmadingen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 597 days.

(21) Appl. No.: 16/344,836

(22) PCT Filed: Oct. 27, 2017

(86) PCT No.: PCT/EP2017/077630
§ 371 (c)(1),
(2) Date: Apr. 25, 2019

(87) PCT Pub. No.: WO2018/091255
PCT Pub. Date: May 24, 2018

(65) Prior Publication Data
US 2019/0247593 A1    Aug. 15, 2019

(30) Foreign Application Priority Data
Nov. 21, 2016 (EP) .................................. 16199873

(51) Int. Cl.
*A61M 11/00* (2006.01)
*B65D 83/20* (2006.01)
(Continued)

(52) U.S. Cl.
CPC ......... *A61M 11/001* (2014.02); *A61M 11/002* (2014.02); *A61M 15/0021* (2014.02);
(Continued)

(58) Field of Classification Search
CPC ............. A61M 11/001; A61M 11/002; A61M 11/006; A61M 11/02; A61M 11/0208;
(Continued)

(56) References Cited

U.S. PATENT DOCUMENTS 3,369,756 A * 2/1968 Ramis ................... B05B 7/0012
239/338
3,371,827 A * 3/1968 Micallef .............. B65D 47/263
222/536
(Continued)

FOREIGN PATENT DOCUMENTS

CN    101384373 A    3/2009
CN    101466613 A    6/2009
(Continued)

OTHER PUBLICATIONS

International Search Report issued in Application No. PCT/EP2017/077630 dated Feb. 21, 2018 and English translation (10 pages).
(Continued)

Primary Examiner — Kathryn E Ditmer
(74) Attorney, Agent, or Firm — Flynn Thiel, P.C.

(57) ABSTRACT

An inhalation device having a reservoir for storing liquid before being discharged, and a discharge head for dispensing the liquid in droplet mist. The discharge head has a nozzle arrangement for generating the droplet mist and housing on which a discharge channel is provided for use as a respiration piece or for attachment of a separate respiration piece. A main axis of extent of the discharge channel encloses an angle of >0° with a central dispensing direction. In alignment with the central dispensing direction of the nozzle arrangement, either an aperture is provided in the housing through which aperture the droplet mist emerges from the discharge head if it is not sucked into the discharge channel by respiration of the user, or a liquid buffer is provided for (Continued)

receiving the droplet mist if it is not sucked into the discharge channel by respiration of the user.

21 Claims, 6 Drawing Sheets

(51) Int. Cl.
| | | |
|---|---|---|
| *A61M 15/00* | (2006.01) | |
| *B65D 83/30* | (2006.01) | |
| *B05B 12/18* | (2018.01) | |
| *A61M 16/12* | (2006.01) | |
| *A61M 16/06* | (2006.01) | |

(52) U.S. Cl.
CPC ............ *A61M 16/12* (2013.01); *B05B 12/18* (2018.02); *B65D 83/205* (2013.01); *B65D 83/30* (2013.01); *A61M 15/009* (2013.01); *A61M 15/0086* (2013.01); *A61M 16/06* (2013.01); *A61M 2202/0468* (2013.01)

(58) Field of Classification Search
CPC ............ A61M 11/08; A61M 15/0065; A61M 15/0086; A61M 15/009; A61M 15/06; B65D 83/205; B65D 83/30; B65D 83/52
See application file for complete search history.

(56) References Cited

U.S. PATENT DOCUMENTS

| | | | | |
|---|---|---|---|---|
| 3,652,015 | A * | 3/1972 | Beall | A61M 16/147 |
| | | | | 261/78.2 |
| 3,756,472 | A | 9/1973 | Vos | |
| 3,884,393 | A | 5/1975 | Wassilieff | |
| 4,067,482 | A | 1/1978 | Vogel et al. | |
| 4,452,239 | A | 6/1984 | Malem | |
| 4,524,888 | A | 6/1985 | Tada | |
| 4,742,927 | A | 5/1988 | Tierney et al. | |
| 4,982,875 | A | 1/1991 | Pozzi et al. | |
| 5,115,803 | A * | 5/1992 | Sioutas | A61M 15/009 |
| | | | | 128/200.23 |
| 5,437,267 | A | 8/1995 | Weinstein et al. | |
| 6,478,199 | B1 * | 11/2002 | Shanklin | B65D 83/265 |
| | | | | 222/207 |
| 6,578,573 | B2 | 6/2003 | Koch | |
| 7,044,341 | B2 * | 5/2006 | Sanchez | B05B 11/0027 |
| | | | | 222/404 |
| 7,530,476 | B2 | 5/2009 | Downey et al. | |
| 7,984,713 | B2 | 7/2011 | Hochrainer et al. | |
| 8,382,010 | B2 | 2/2013 | Nadler et al. | |
| 8,490,837 | B2 * | 7/2013 | Michaux | B05B 11/306 |
| | | | | 222/321.9 |
| 8,870,844 | B2 | 10/2014 | Perovitch et al. | |
| 9,108,782 | B2 * | 8/2015 | Luc | A61L 9/12 |
| 9,598,225 | B2 | 3/2017 | Patil et al. | |
| 2005/0183718 | A1 | 8/2005 | Wuttke et al. | |
| 2007/0246484 | A1 * | 10/2007 | Yoshida | B05B 11/3059 |
| | | | | 222/384 |
| 2008/0041375 | A1 | 2/2008 | Stratton | |
| 2010/0089950 | A1 | 4/2010 | Helf et al. | |
| 2011/0290244 | A1 * | 12/2011 | Schennum | A24F 42/60 |
| | | | | 128/200.23 |
| 2013/0333709 | A1 * | 12/2013 | Shimizu | A24F 7/02 |
| | | | | 131/223 |
| 2015/0040893 | A1 * | 2/2015 | Besseler | A61M 11/007 |
| | | | | 128/200.21 |
| 2015/0284177 | A1 | 10/2015 | Patil et al. | |
| 2016/0325916 | A1 * | 11/2016 | Jasper | B65D 83/22 |
| 2017/0021116 | A1 * | 1/2017 | Rahmel | B65D 83/22 |
| 2017/0036226 | A1 * | 2/2017 | Goettke | B05B 15/65 |
| 2018/0117267 | A1 * | 5/2018 | Nadler | A61M 16/201 |
| 2019/0201639 | A1 | 7/2019 | Lutz et al. | |

FOREIGN PATENT DOCUMENTS

| | | |
|---|---|---|
| CN | 102413945 A | 4/2012 |
| CN | 203400384 U | 1/2014 |
| EP | 1022235 A1 | 7/2000 |
| EP | 1 743 671 A1 | 1/2007 |
| EP | 1754542 A2 | 2/2007 |
| EP | 3 095 522 A1 | 11/2016 |
| EP | 3275492 A1 | 1/2018 |
| EP | 3275555 A1 | 1/2018 |
| EP | 3275558 A1 | 1/2018 |
| FR | 2723926 A1 | 3/1996 |
| JP | 200148254 A | 2/2001 |
| WO | 02/074372 A2 | 9/2002 |
| WO | 2005/084735 A1 | 9/2005 |
| WO | 2009/023210 A1 | 2/2009 |
| WO | 2010/103227 A1 | 9/2010 |
| WO | 2011147714 A1 | 12/2011 |
| WO | 2014/140774 A1 | 9/2014 |
| WO | 2015/149922 A2 | 10/2015 |
| WO | 2015/155606 A2 | 10/2015 |
| WO | WO-2015149922 A2 * | 10/2015 ........ A61M 15/0073 |

OTHER PUBLICATIONS

Written Opinion issued in Application No. PCT/EP2017/077630 dated Feb. 21, 2018 (16 pages).
European Patent Office Search Report issued in Application No. EP 16199873.7, with English translation of category of cited documents, dated Aug. 2, 2017 (5 pages).
Office Action of European Patent Office issued in corresponding European Patent Application No. 16 199 873.7 dated Sep. 7, 2020 (12 pages).
Chinese Office Action with partial English Translation issued in corresponding Chinese Application No. 201780071999.0 dated Jan. 6, 2021 (14 pages).

* cited by examiner

INHALATION DEVICE FOR THE PURPOSE OF INHALATION OF A DROPLET MIST

FIELD OF APPLICATION AND PRIOR ART

The invention relates to an inhalation device for the purpose of inhalation of a droplet mist by a user.

Inhalation devices of this kind serve the purpose of delivering a liquid in atomized form to the airways and lungs of the user. The liquid used in them is a pharmaceutical liquid that serves to alleviate respiratory tract disorders and breathing problems. The liquid may contain active pharmaceutical ingredients or may, for example like saline, be designed to contribute to alleviating the disorders without containing such active substances.

The invention relates in particular to mobile inhalation devices in which the liquid is pressurized manually or by a pressure accumulator and is fed to a nozzle arrangement that generates the droplet mist.

An inhalation device of the type in question is known from EP 3095522 A1, published subsequently. An important problem with the inhalation device of the type in question lies in generating and delivering sufficiently fine droplets in the droplet mist. In the case of nozzle arrangements that generate a droplet mist without using mechanically movable parts, the droplet size depends crucially on the pressure of the liquid delivered. In the specific case of the aforementioned mobile inhalation devices, which are used portably and without electrical assemblies and in which it is difficult to achieve a pressure of the delivered liquid of above 5 bar, it is only with difficulty that these generate droplets that can access the airways. A further problem is that, on account of the air resistance, the released droplets of the generated droplet mist tend to agglomerate into larger droplets even before they have reached the airways.

PROBLEM AND SOLUTION

The problem addressed by the invention is to develop an inhalation device of the type in question in such a way that it is able to generate a droplet mist composed of sufficiently fine droplets. A further problem addressed is to make available a design of an inhalation device that allows the inhalation device to be easily adapted, particularly also in respect of different dispensing modes and/or the respectively desired droplet size.

To this end, an inhalation device is proposed which comprises a liquid reservoir for storing liquid before the latter is discharged, and a discharge head for dispensing the liquid in the form of the droplet mist. The discharge head has an outer housing, and a nozzle arrangement for generating the droplet mist in the form of a spray jet.

A discharge channel for use as a respiration piece or for attachment of a separate respiration piece is provided on the outer housing.

The main axis of extent of the discharge channel encloses an angle of >0° with a central dispensing direction of the nozzle arrangement, preferably a greater angle of at least 15°. In alignment with the central dispensing direction of the nozzle arrangement, an aperture is provided in the outer housing, or a liquid buffer is provided.

The aperture in the outer housing of the discharge head means that the droplet mist from the discharge head can pass through this aperture if it is not sucked into the discharge channel by respiration of the user, wherein the aperture is adapted to the nozzle arrangement, and to the spray jet generated by the latter, in such a way that at least most of the spray jet can emerge through the aperture. Alternatively to this, the liquid buffer for receiving the droplet mist is likewise provided in alignment with the dispensing direction.

In an inhalation device according to the invention, provision is therefore made that the droplet mist generated by the nozzle arrangement does not flow directly into a linear discharge channel at the end of which the user is intended to breathe in. Instead, the discharge channel is at an angle to the dispensing direction. Instead, either said aperture or said liquid buffer is provided in alignment with the emerging droplet mist.

This design has several advantageous effects. If the user interrupts the breathing-in process in order to exhale, liquid can still be atomized through the nozzle arrangement. However, this then emerges either through the aperture into a surrounding atmosphere or is delivered to a liquid buffer which, for example, can be formed by a pore-like structure and stores the liquid temporarily until its evaporation.

Therefore, the liquid atomized during the interruption in the breathing process does not collect in an uncontrolled manner on the inner faces of the outer housing, and instead it is either released through the aperture or stored in the liquid buffer, such that it can then evaporate from here. In the case of an aperture, the clear cross section of the aperture is adapted to the nozzle arrangement spacing and to the opening angle of the spray jet in such a way that at least most of the liquid in droplet form can emerge directly through the aperture. The aperture is preferably dimensioned in such a way that most (>90%) of the liquid or even all of the liquid can emerge in droplet form directly through the aperture. However, it is also considered advantageous if the aperture is not substantially larger than is necessary for the purpose, as will be explained further below.

The second main effect of the proposed structure is obtained through the angled setting of the discharge channel relative to the dispensing direction. When breathing in, the user generates an air flow that is at an angle to the dispensing direction of the nozzle arrangement and thereby causes the droplets to burst when they enter the eddy thus generated. The aperture mentioned, which can serve to discharge the droplet mist during interruptions in the user's breathing, can act as an inflow opening during inhalation by the user. The air flowing in here bursts open the droplets, in the manner already described, and thus leads to a finer droplet mist.

The proposed arrangement is also advantageous for the reason that it allows the individual droplets of the mist to be deflected differently depending on their size. This may be expedient if a nozzle arrangement is used that leads to a strongly non-uniform size of droplets. In such a case, it may be desirable to convey only the finer droplets into the discharge channel, while the larger droplets are not inhaled. The aforementioned angled setting achieves this aim, since larger droplets are subject to a lesser extent to the eddy effect during the inhalation process.

A main axis of the inhalation device can be formed by a main rotation axis, about which the discharge head is rotatable relative to the liquid reservoir, and/or by a rotationally symmetrical configuration of the bottle-like liquid reservoir. When reference is made hereinbelow to the main axis, this is alternately the main rotation axis or the axis of symmetry. Of particular advantage is a configuration in which these axes are identical.

Said main axis, on the one hand, and the main axis of extent arranged centrally in the discharge channel are arranged and oriented in such a way that they do not intersect.

The stated design of the inhalation device with the described main axis is considered advantageous. This main axis is preferably both the main rotation axis, about which the discharge head is rotatable relative to the liquid reservoir, and also the central axis of the at least in part rotationally symmetrical liquid reservoir. Said eccentric arrangement of the discharge channel is of advantage, particularly if the dispensing direction is also angled relative to the main axis. Here, an angle of between 75° and 105° is in particular deemed advantageous between the central dispensing direction of the nozzle arrangement and the main axis, in particular preferably a right angle.

The main axis and the main axis of extent of the discharge channel preferably enclose an angle of between 45° and 135°, wherein the angle is preferably between 90° and 135° when the discharge channel is oriented facing away from the liquid reservoir.

The angle between the preferably mutually skewed axes of the main axis and the main axis of extent of the discharge channel is the angle by which the discharge channel is angled relative to the vertical when the main axis and thus the inhaler as a whole is oriented vertically. The particularly preferred range of between 90° and 135° means that, with the inhalation device oriented vertically, the discharge channel is oriented horizontally or points upward at a slight inclination with respect to the discharge direction, such that the user can easily hold the inhaler below mouth height in order to be able to breathe in at the distal end of the discharge channel, if appropriate with his head inclined slightly forward.

The main axis of extent of the discharge channel encloses an angle of between 15° and 120°, in particular preferably of between 45° and 100°, with the central dispensing direction of the nozzle arrangement.

This angle between the main axis of extent of the discharge channel and the central dispensing direction of the nozzle arrangement is the angle about which the droplet mist is deflected during the inhalation by the user. The ideal value results in each case according to the droplet size generated by the nozzle arrangement and the droplet size intended to be inhaled. It may therefore be expedient to configure an otherwise identical inhalation device with different angles depending on the purpose for which it is used. The modularity described hereinbelow, with outer housing and inner housing, is also to be understood in this light.

In addition to the discharge channel, an inflow channel can be provided in the outer housing, which inflow channel is spaced apart from the aperture aligned with the dispensing direction of the nozzle arrangement and from the liquid buffer aligned with the discharge direction of the nozzle arrangement. A plurality of such additional inflow channels may also be expedient. The air can be sucked in through these when the user breathes in through the discharge channel. Particularly in a design with a liquid buffer, it is advantageous if a separate inflow channel is provided in the outer housing, through which the air needed to deflect the droplet mist can flow into the outer housing. However, in the design of the discharge head with the aperture aligned with the dispensing direction of the nozzle arrangement, it may also be advantageous to provide one or more of these further separate inflow channels in order to advantageously influence the inward flow of the droplet mist.

As has been explained above, the aperture is dimensioned such that most of the liquid stream in droplet form can flow out collision-free through the aperture in the dispensing direction defined by the nozzle arrangement, when the user does not suck air in at the distal end of the discharge channel. This preferably applies for the entire liquid stream.

However, it is considered advantageous if the aperture is not much larger than is necessary for this purpose. Therefore, the cross-sectional surface area of the spray jet intersecting the outer housing in the region of the aperture preferably occupies at least 30% of the free section formed in the outer housing by the aperture. Particularly preferably, the cross-sectional surface area occupies at least 50% or even at least 70% of the free section. The imaginary cross-sectional surface area through the usually more or less conical spray jet, at which the latter breaks through the free section generated in the housing by the aperture, accordingly takes up a considerable part of the free section. This is advantageous in preventing a situation where too much air flows in externally of the spray jet, since this air, depending on the design, could have an effect opposite to the desired effect, by promoting an enlargement of the droplets rather than bursting them. Moreover, it is expedient for the aperture to be kept as small as possible so as to increase the flow velocity.

The nozzle arrangement is in particular designed to generate a spray jet whose angle of opening is less than 30°, preferably less than 15°.

Furthermore, a design of an inhalation device is proposed in which the inhalation device comprises a base having a liquid reservoir for storing liquid before the latter is discharged, and a discharge head for dispensing the liquid in the form of a droplet mist. The discharge head has a nozzle arrangement for generating the droplet mist. The inhalation device comprises a switching valve, by means of which a delivery channel from the liquid reservoir to the nozzle arrangement can be opened and closed.

The discharge head is rotatable relative to the base about a main rotation axis, by which means the switching valve can be opened and closed.

The discharge head provided here comprises an inner housing which is connected to the base and on which the nozzle arrangement is provided for dispensing the droplet mist in a dispensing direction at an angle to the main rotation axis, and an outer housing which can be placed onto the inner housing in a defined rotation position. The inner housing and the outer housing interact with a form-fit engagement in respect of a rotation about the main rotation axis such that a rotational movement of the outer housing relative to the base can also directly effect a rotational movement of the inner housing relative to the base.

The outer housing has a discharge channel which is designed for use as a respiration piece or for attachment of a respiration piece and which, when the outer housing is fitted, is arranged relative to the nozzle arrangement in such a way that the droplet mist dispensed from the nozzle arrangement can be inhaled through the discharge channel.

The second described way of configuring an inhalation device according to the invention is preferably used jointly with the features already described above. In principle, however, a configuration of the inhalation device may also be expedient that does not have the key features of the first type explained above.

The particular aspect of this second preferred configuration is that the discharge head has an inner housing which also comprises the nozzle arrangement. This inner housing is rotatable relative to the base of the inhalation device for opening and closing said switching valve. Provision is thus made that the inner housing initiates the discharge process by being rotated relative to the base and ends the discharge process again by being rotated in the opposite direction.

The outer housing is preferably pushed onto the inner housing in the above-described direction of the main axis, wherein an inlet aligned with the dispensing direction of the nozzle arrangement is provided on the inner face of the outer housing and leads into the discharge channel, at the distal end of which the user sucks in order to perform the inhalation.

The modularity achieved by this configuration of the inner housing and outer housing affords a number of advantages. On the one hand, it is possible at the place of manufacture to use different outer housings depending on the medium that is to be discharged. Since the outer housing is preferably the component which, by its design, defines the aforementioned angled setting between the dispensing direction and the direction of the discharge channel, this angle can be varied through the choice of several possible outer housings. The stated modularity also makes it possible, depending on the purpose of use and in particular on the symptoms of the user, to alternately use a breathing mask or a mouthpiece, which are integrally formed on the outer housing. However, this flexibility can also be achieved by a multi-part design of the outer housing, which is explained in detail below.

The inner housing and the outer housing preferably have mutually interacting clamping regions on the inside of the outer housing and on the outside of the inner housing, in the region of which they can be pushed into each other and held with force-fit engagement in order to produce an interference fit. The stated clamping regions preferably lead to a peripheral clamping between inner housing and outer housing, such that, on the one hand, air cannot penetrate here and, on the other hand, the outer housing is prevented from falling off.

The outer housing preferably has a jacket surface. The outer face of this jacket surface can be provided with a channel connector which forms the discharge channel, and of which the main axis of extent is at an angle with respect to the central dispensing direction of the nozzle arrangement. A wall of the channel connector is preferably provided with the aperture in alignment with the dispensing direction of the nozzle arrangement. Said channel connector is therefore preferably provided asymmetrically on the outer housing and in particular can preferably have a more or less tangential orientation.

A liquid-receiving space is preferably provided for receiving liquid that settles internally on the outer housing after being dispensed through the nozzle arrangement. Such a liquid-receiving space serves the purpose of allowing deposited liquid to automatically collect here and of preventing it from flowing out. For this purpose, the liquid-receiving space is preferably provided as a kind of recessed receiving region when the inhalation device is held in the usual way with the discharge head pointing upward and the liquid reservoir pointing downward.

In particular, the liquid-receiving space can be formed jointly by an inner wall of the outer housing and an outer wall of the inner housing. It is considered advantageous if the liquid-receiving space is configured as an annular space. The use of a liquid-receiving space delimited jointly by the outer housing and the inner housing leads to very simple emptying of this liquid-receiving space. If, after use of the inhalation device, the outer housing is detached from the inner housing, the liquid-receiving space is thus also opened, such that the excess liquid can be deliberately poured off.

The channel connector, which forms the discharge channel, can open out in a mouthpiece or in a breathing mask. Alternatively, a mouthpiece separate from the channel connector or a separate breathing mask can be provided for coupling to the channel connector. If the discharge channel is designed as a mouthpiece, it preferably has a cross-sectional surface area deviating from a circular cross section, in particular an approximately oval or otherwise elongate shape that can be easily enclosed by the lips. Given the possibility of using a separate mouthpiece or a separate breathing mask as a respiration piece which can be connected to the channel connector in particular by means of a plug-in connection, it is possible to produce an optimal configuration according to the specific case of use and/or the symptoms of the user.

The liquid reservoir is preferably configured as a pressure accumulator in which the liquid is kept at an overpressure. It is preferably configured to receive at most 500 ml of liquid, particularly preferably at most 250 ml. The use of a pressure accumulator is advantageous since in this way comparatively high pressures can be generated, and these are in particular available independently of the user. A system is considered particularly advantageous in which the pressure accumulator contains a liquid bag, the outside of which is subjected to pressure by compressed air. Alternative configurations are also possible in which pressure is applied by the user.

The stated receiving volume of the liquid reservoir is the volume that is considered to be particularly expedient in mobile inhalation devices.

The nozzle arrangement can have a nozzle plate with a plurality of nozzle openings for generating the droplet mist. Such a nozzle arrangement with a nozzle plate represents a particularly simple way of generating a droplet mist. It is preferably a silicon plate. Moreover, the number of the nozzle openings is preferably in excess of 10 nozzle openings, for example 20 or more nozzle openings, the diameter of the nozzle openings preferably being in the range between 2 μm and 200 μm.

Although such a nozzle plate is considered to be very advantageous for generating the droplet mist, other configurations are also possible. In particular, these also include the use of a vortex chamber into which the liquid flows in such a way that a swirling motion develops, by which the liquid is torn into individual droplets as it emerges. Although with such a technique it is possible only with difficulty to achieve a droplet formation in which the droplets are sufficiently accessible to the airways, the described deflection of the droplet mist and the refinement associated therewith make it possible to use this technique in an inhalation device.

For the purpose of opening and closing the switching valve, the discharge head is preferably movable relative to the base in a superposed rotational and axial movement. To this end, a slotted guide, with a slot having the shape of part of a helix, is in particular preferably provided between the base and the discharge head. This construction is a particularly simple and interference-free way of utilizing a rotational movement of the discharge head relative to the base in order to open and close a valve. The switching valve can be configured in such a way that it is opened and closed by an axial movement. Through the enforced superposition of a rotational movement and an axial movement, said rotational movement then leads to the opening or closing.

The liquid reservoir of the described inhalation device is preferably filled with one of the following liquids: a saline aqueous solution, an aqueous solution in the form of a Ringer's solution or a buffered solution, an aqueous solution with at least one of the additives carbohydrates, essential oils, menthol and plant extracts, an aqueous solution containing vitamins, trace elements, manganese or zinc, or an aqueous solution with at least one of the additives from the group comprising cinnamon oil, tea tree oil, sage oil, thyme oil, lemon balm.

BRIEF DESCRIPTION OF THE DRAWINGS

Further advantages and aspects of the invention will become clear from the claims and from the following description of preferred illustrative embodiments of the invention, which are explained below with reference to the figures.

DETAILED DESCRIPTION OF THE ILLUSTRATIVE EMBODIMENTS

Figure 1:
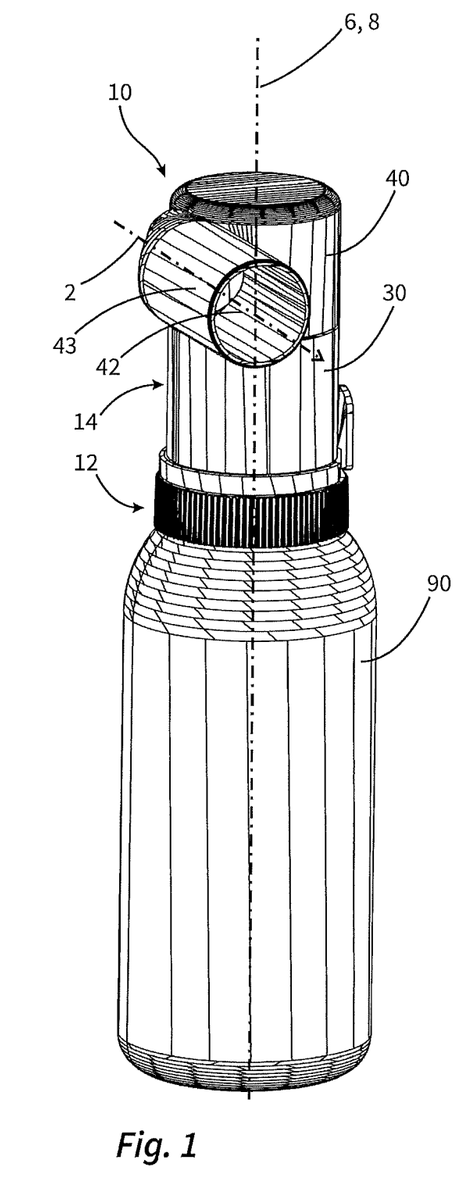
FIGS. 1 and 2 show an inhalation device according to the invention in an overall view and in a sectioned view.
Figure 2:
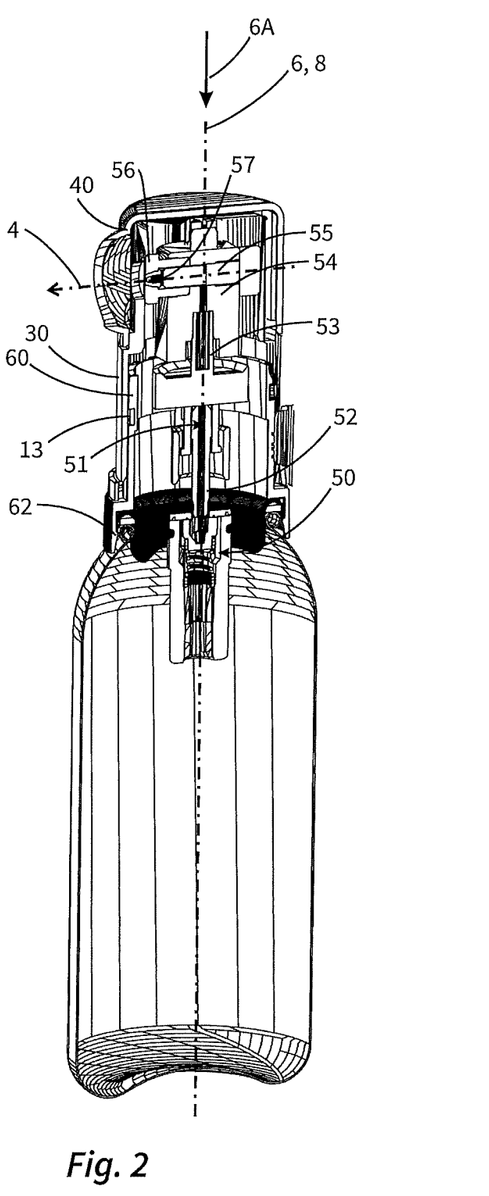
Figure 3:
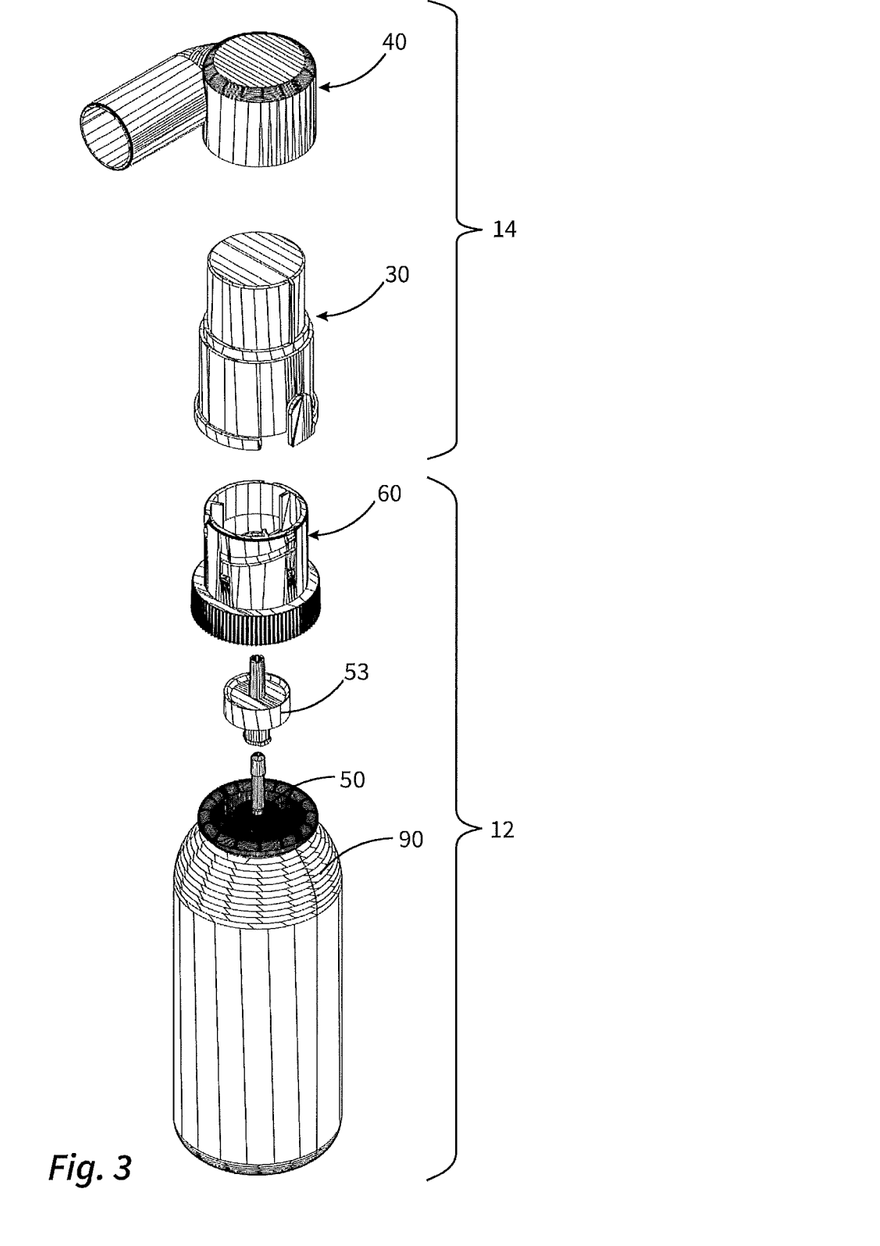
FIG. 3 shows the components of the inhalation device in an exploded view.
Figure 4:
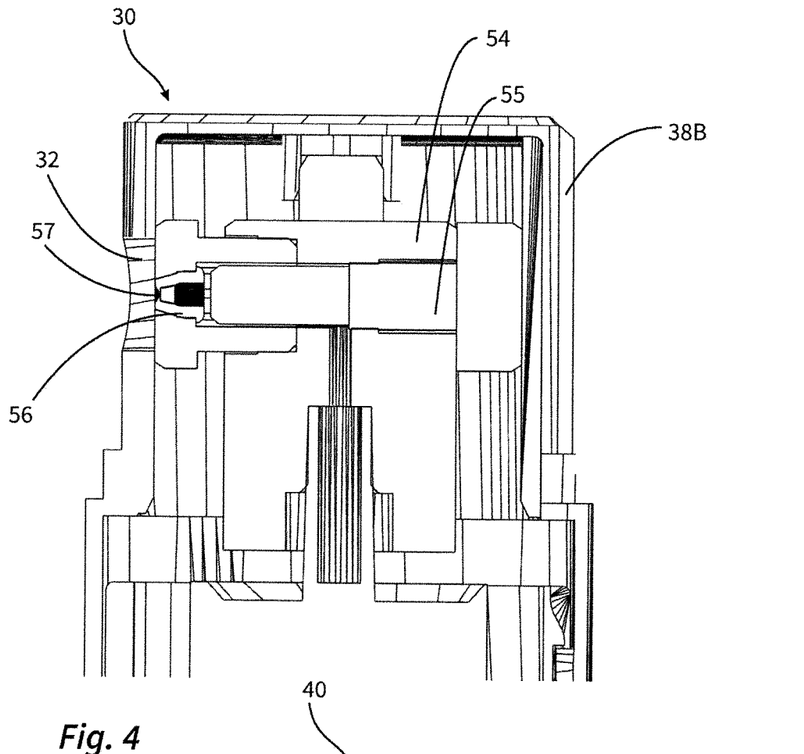
FIGS. 4 and 5 show details of the discharge head.
Figure 5:
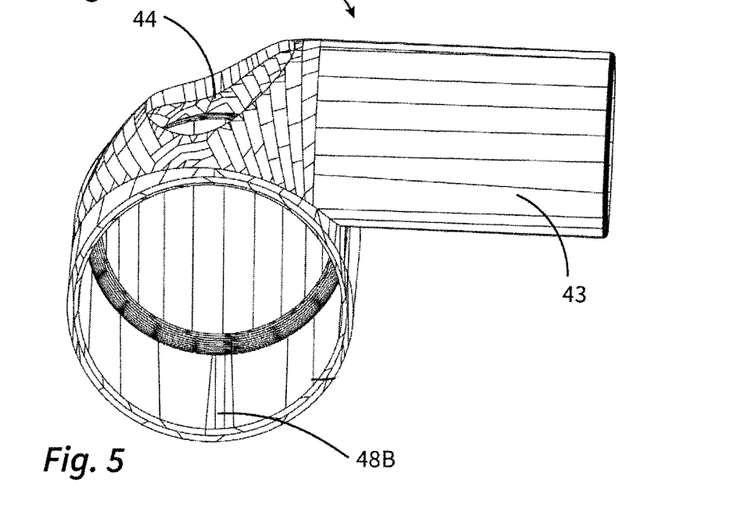

FIGS. 1 and 2 show an inhalation device 10 according to the invention, on the one hand in an overall view and on the other hand in a sectioned view. Referring also to FIG. 3, the inhalation device 10 has a base 12, and a discharge head 14 which is rotatable relative to the base 12 about a main rotation axis 6.

The main constituent parts of the base 12 are a liquid reservoir 90 with an outlet-side switching valve 50, which can be opened by movement of a tappet 52 in the direction of the arrow 6A. The liquid reservoir 90 is designed in the manner of a squeeze bottle with rotational symmetry about a central axis 8. The base 12 furthermore comprises a base component 60 which is snap-fitted by locking means 62 onto the liquid reservoir 90 configured as the squeeze bottle.

The discharge head 14 has, as its main constituent parts visible from the outside, an inner housing 30 and an outer housing 40, wherein the inner housing 30 is only partially covered by the outer housing 40. Provided inside the inner housing 30 are a plurality of structural parts 54, 55 for conveying liquid, and also a nozzle arrangement 56 which has a nozzle plate 57 made of silicon with a multiplicity of nozzle openings (not shown in detail).

As will be seen in particular from FIG. 2, the dispensing direction 4 of the nozzle arrangement 56 encloses a right angle with the main rotation axis 6 of the inhalation device 10 and with the central axis 8 of the liquid reservoir.

For the purpose of actuating the switching valve 50, a slotted guide 13 is provided, of which the slot, having the shape of part of a helix, can be seen from FIG. 3. A cam on the inner face of the inner housing 30 engages in this slot in such a way that a rotational movement of the discharge head 14 relative to the base 12 also directly effects an axial movement of the discharge head 14 relative to the base 12, such that, by means of an intermediate structural part 53, the tappet 52 can be pressed down by this rotational movement and the switching valve 50 can be opened.

As will be seen from FIG. 1, the outer housing 40 has a channel connector 43 which is oriented in a main axis of extent 2 and forms a discharge channel 42 that is oriented eccentrically with respect to the main rotation axis 6. This discharge channel 42 serves for the inhalation, by means of the user sucking in at its distal end.

Once the user has first of all initiated the discharge process using the described rotational movement, this inhalation takes place such that liquid from the liquid reservoir 90 flows through the liquid channel 51 as far as the nozzle arrangement 56 and is atomized there. The opening and closing of the switching valve preferably takes place by means of the user fixing the channel connector 43, or a respiration piece mounted thereon, with his mouth or part of his face and then rotating the liquid reservoir 90 about the main rotation axis 6.

To ensure that the outer housing 40 and the inner housing 30 rotate jointly, they are connected to each other with form-fit engagement. Referring to FIGS. 4 and 5, it will be seen that a form-fit web 38B is provided on the inner housing 30 and interacts with a corresponding groove 48B on the outer housing 40.

It is important to note that this specific configuration is just an example. In a configuration of outer housing 40 and inner housing 30 that also takes account of esthetic points of view, these housings are preferably configured overall in such a way as to achieve the desired rotationally fixed form-fit engagement.

The function and special nature of the discharge head 14 are explained with reference to FIGS. 6A to 6C. For this purpose, the discharge head 14 is shown in section along a horizontal plane at the level of the nozzle arrangement 56.

FIG. 6A shows the starting state. The user places the channel connector 43 in his mouth or fixes it in some other way by means of a respiration piece attached thereto. The liquid reservoir 90 is then rotated as illustrated by the arrow 6B, such that the discharge head 14 and the base 12 approach each other axially on account of the slotted guide 13, and the discharge head 14 indirectly presses the tappet 52 down and thereby opens the switching valve 50. The liquid now flows along the liquid channel 51 as far as the nozzle arrangement 56 and is there converted, in the manner illustrated by FIG. 6B, into a spray mist of small droplets.

As FIG. 6B shows, this spray mist can emerge directly from the discharge head 14 through an aperture 44 in alignment with the nozzle arrangement 56. Therefore, there is no relevant wetting of the inner faces of the discharge head.

When the user now starts the inhalation process by sucking on the distal end of the channel connector 43, the situation illustrated in FIG. 6C is obtained. Most of the droplets of the droplet mist 100 are deflected and then flow in the direction of the main axis of extent 2 of the discharge channel 42. The deflection causes the droplets to burst, with the result that the mean droplet diameter decreases significantly. As is likewise illustrated by FIG. 6C, droplets that are too large and are unsuitable for the inhalation are deflected to a lesser extent, such that they do not enter the channel connector 43. During the inhalation process, the air required for refining the droplet mist 100 flows in through the aperture 44.

As soon as the user ends the inhalation process, the situation according to FIG. 6B is obtained again. If the user breathes out through the inhalation device 10, the exhaled air flows through the aperture 44 and out of the outer housing 40 together with the spray jet.

FIG. 7 illustrates that, regarding the undeflected spray jet, the cross-sectional surface area 100A thereof in the region of the aperture 44 considerably fills, preferably by more than 50%, the free section 44A formed by the aperture 44. Although not absolutely necessary, it is nevertheless considered advantageous to obtain such a high degree of filling, since this ensures that most of the inflowing air participates in the deflection of the droplet mist 100. Moreover, a comparatively small aperture 44 leads to a higher flow velocity of the inflowing air and therefore to improved atomization with smaller droplets.

Figure 8A:
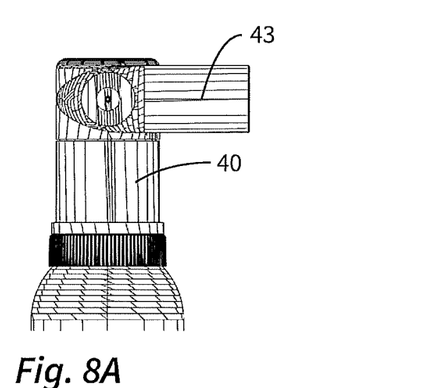
FIGS. 8A to 8C show alternative possibilities concerning the design of the respiration piece of the inhalation device.
Figure 8B:
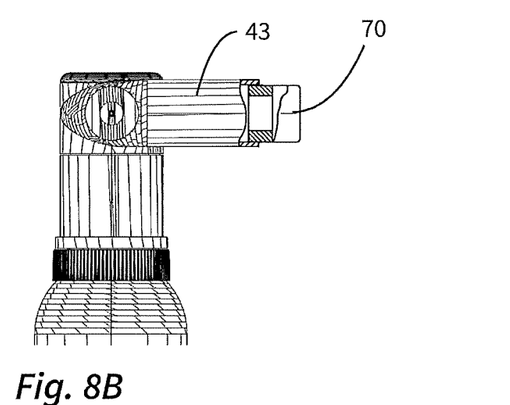
Figure 8C:
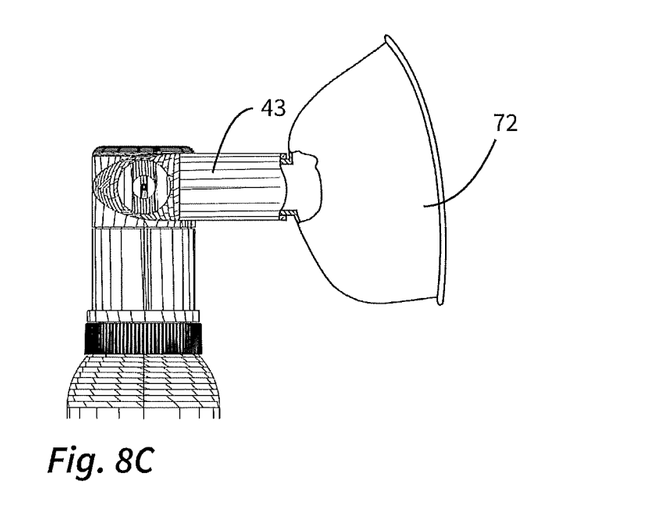

FIGS. 8A to 8C illustrate possible configurations of the inhalation device 10 with a respiration piece.

FIG. 8A corresponds to the configuration in the preceding figures. Here, provision is made that the channel connector 43 is used directly as a mouthpiece by the user, i.e. is intended to be enclosed by the lips during inhalation. FIG. 8B shows that it is instead also possible to use an insert in the form of a separate mouthpiece 70, for example in order thereby to permit hygienic use of the inhaler by several persons. As an alternative to the mouthpiece 70, it is also possible to use a separate breathing mask 72 in the manner seen from FIG. 8C.

Figures 6A, 6B, 6C:
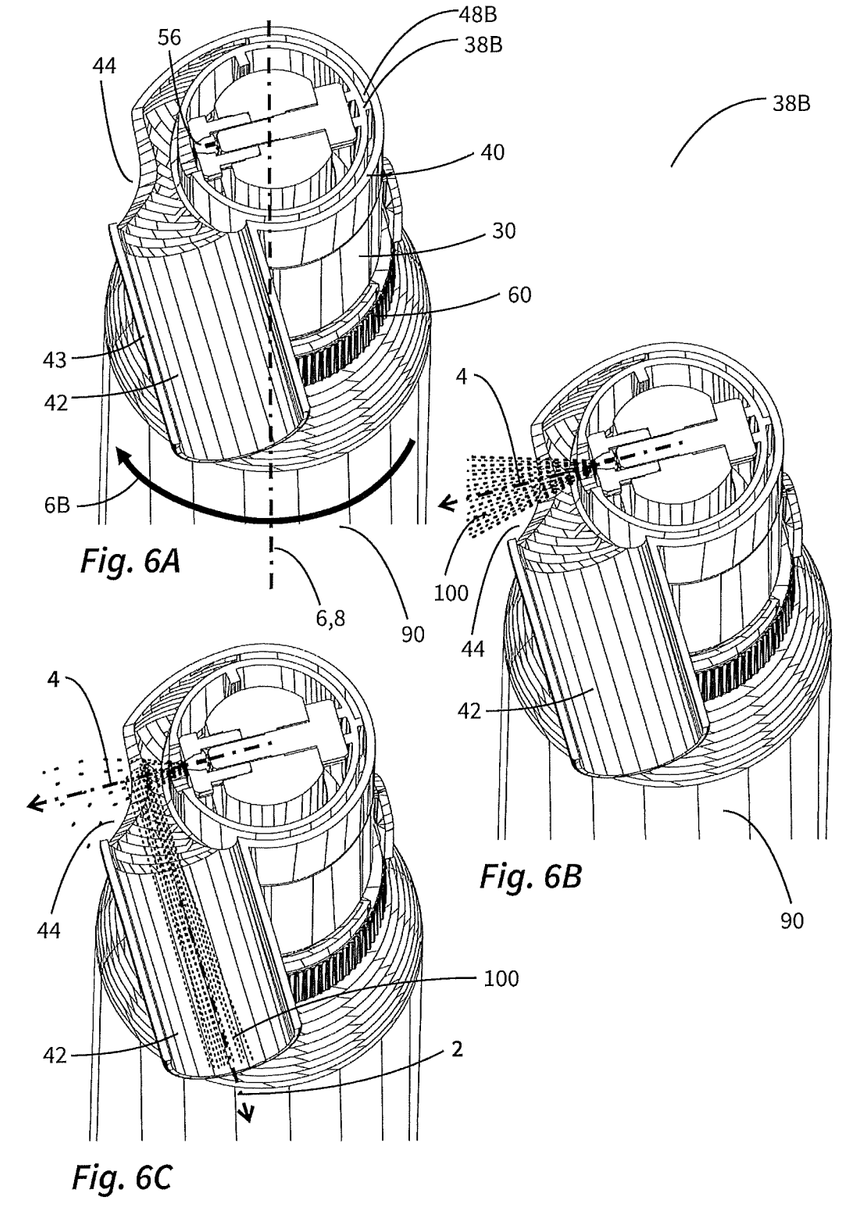
FIGS. 6A to 6C illustrate the way in which the inhalation device functions.
Figure 7:
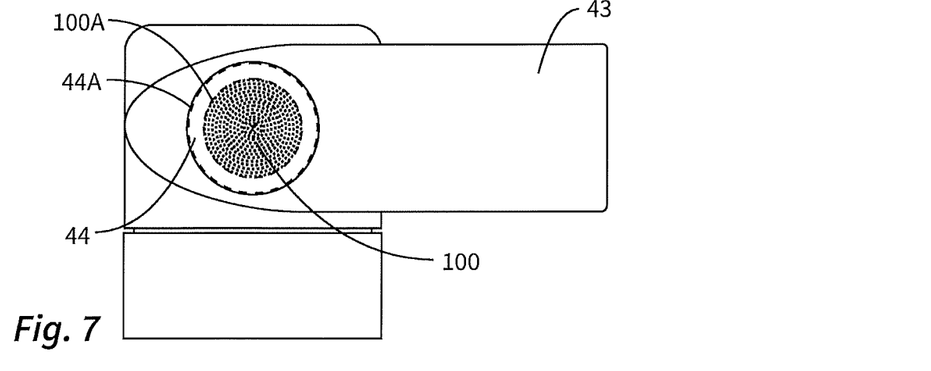
FIG. 7 shows the spray jet of the inhalation device in relation to the aperture provided for the discharge in the outer housing of the discharge head.
Figure 9:
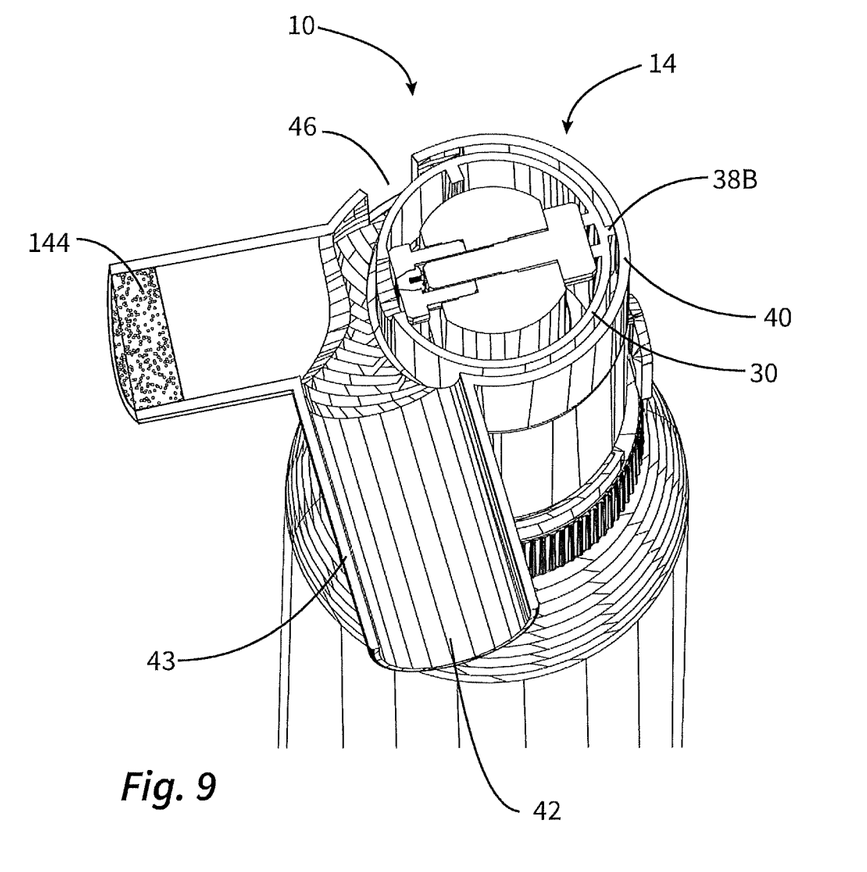
FIG. 9 shows an alternative configuration of the discharge head.

FIG. 9 shows an alternative configuration of the inhalation device 10. Here, the outer housing 40 has a slightly different form. Instead of an aperture 44 which connects directly to a surrounding atmosphere, use is here made of a sponge-like or porous liquid buffer 144. If the inhalation is interrupted after the start of the discharge process, in accordance with FIG. 6B, the spray jet is directed to this liquid buffer 144 and can be received there. After completion of the inhalation, the liquid can then evaporate from here. Since the liquid buffer in the illustrated configuration is not easily suitable for use as an inflow channel, the configuration in FIG. 9 is provided with a separate inflow channel 46.

The invention claimed is:

1. An inhalation device for the purpose of inhalation of a droplet mist by a user, comprising-:
    a base having a liquid reservoir for storing liquid before the liquid is discharged;
    a discharge head for dispensing the liquid in the form of a droplet mist, the discharge head having a nozzle arrangement for generating the droplet mist;
    a switching valve, wherein a delivery channel from the liquid reservoir to the nozzle arrangement is opened and closed via the switching valve;
    the discharge head being rotatable relative to the base about a main rotation axis, wherein the switching valve is opened and closed via rotation of the discharge head relative to the base about the mail rotation axis;
    the discharge head comprising an inner housing connected to the base, the nozzle arrangement being provided on the inner housing for dispensing the droplet mist in a dispensing direction at an angle to the main rotation axis;
    the discharge head comprising an outer housing placed onto the inner housing;
    the inner housing and the outer housing interacting with a form-fit engagement in respect of a rotation about the main rotation axis, such that a rotational movement of the outer housing relative to the base also directly effects a rotational movement of the inner housing relative to the base; and
    the outer housing has a portion forming a discharge channel, the portion being configured for use as a respiration piece or for attachment of a respiration piece, the discharge channel, when the outer housing is fitted to the inner housing, is arranged relative to the nozzle arrangement in such a way that the droplet mist dispensed from the nozzle arrangement is inhaled through the discharge channel, and the main rotation axis and a main axis of extent arranged centrally in the discharge channel are arranged in such a way that they do not intersect.

2. The inhalation device as claimed in claim 1, wherein the liquid reservoir has a central axis and a configuration rotationally symmetrical in relation to a central axis, and the central axis and the main axis of extent are arranged such that they do not intersect.

3. The inhalation device as claimed in claim 2, wherein the main rotation axis and/or the central axis and the main axis of extent of the discharge channel enclose an angle of between 45° and 135°.

4. The inhalation device as claimed in claim 1, wherein the main axis of extent of the discharge channel encloses an angle of between 15° and 120° with the dispensing direction of the nozzle arrangement.

5. The inhalation device as claimed in claim 4, wherein the main rotation axis and the dispensing direction of the nozzle arrangement enclose an angle of between 75° and 105°.

6. The inhalation device as claimed in claim 1, wherein the inner housing and the outer housing have mutually interacting clamping regions on an inside of the outer housing and on an outside of the inner housing, in a region of which clamping regions the inner housing and the outer housing are pushed into each other and held with a force-fit engagement in order to produce an interference fit.

7. The inhalation device as claimed in claim 1, wherein the portion of the outer housing comprises a channel connector provided externally on the outer housing and forming the discharge channel, and the main axis of extent of the discharge channel is at an angle with respect to the dispensing direction of the nozzle arrangement.

8. The inhalation device as claimed in claim 7, wherein the channel connector has a wall, the wall having an aperture therein disposed in alignment with the dispensing direction of the nozzle arrangement.

9. The inhalation device as claimed in claim 8, wherein in addition to the discharge channel, an inflow channel is provided in the outer housing, the inflow channel being spaced apart from the aperture, the inflow channel being configured such that air is sucked in through the inflow channel when the user breathes in through the discharge channel.

10. The inhalation device as claimed in claim 1, further comprising a liquid-receiving space for receiving liquid that settles internally on the outer housing after being dispensed through the nozzle arrangement.

11. The inhalation device as claimed in claim 10, wherein:
    when the inhalation device is oriented in an intended orientation with the discharge head facing upward and the liquid reservoir facing downward, the liquid-receiving space is provided as a recessed receiving region such that, in the intended orientation, no liquid collected in the recessed receiving region runs out of the discharge head; and/or
    the liquid-receiving space is formed jointly by an inner wall of the outer housing and an outer wall of the inner housing; and/or
    the liquid-receiving space is configured as an annular space.

12. The inhalation device as claimed in claim 1, wherein the portion of the outer housing comprises a channel connector, the channel connector forming the discharge channel, wherein the channel connector:

terminates in a mouthpiece or in a breathing mask; or the inhalation device comprises a mouthpiece separate from the channel connector or a breathing mask for coupling to the channel connector.

13. The inhalation device as claimed in claim 1, wherein:

the liquid reservoir is configured as a pressure accumulator in which the liquid is kept at an overpressure; and/or the liquid reservoir is configured to receive at most 500 ml of liquid.

14. The inhalation device as claimed in claim 1, wherein the nozzle arrangement has a nozzle plate with a plurality of nozzle openings.

15. The inhalation device as claimed in claim 1, wherein, for the purpose of opening and closing the switching valve, the discharge head is movable relative to the base in a superposed rotational and axial movement.

16. The inhalation device as claimed in claim 15, further comprising a slotted guide, the slotted guide including a slot having the shape of a part of a helix, the slot being provided between the base and the discharge head.

17. The inhalation device as claimed in claim 1, wherein the liquid reservoir is filled with:

a saline aqueous solution; or an aqueous solution in the form of a Ringer's solution or a buffered solution; or an aqueous solution with at least one of the following additives: carbohydrates; essential oils; menthol; and/or plant extracts; or an aqueous solution containing vitamins, trace elements, manganese or zinc; or an aqueous solution with at least one of the following additives: cinnamon oil; tea tree oil; sage oil; thyme oil; and/or lemon balm.

18. The inhalation device as claimed in claim 1, wherein the main axis of extent of the discharge channel encloses an angle of >0° with the dispensing direction of the nozzle arrangement, and an aperture is provided in the outer housing of the discharge head in alignment with the dispensing direction of the nozzle arrangement, through which aperture the droplet mist in the form of a spray jet emerges from the discharge head if the spray jet is not sucked into the discharge channel by respiration of the user, wherein the aperture is adapted to the nozzle arrangement and to the spray jet generated by the nozzle arrangement in such a way that at least most of the spray jet emerges through the aperture.

19. The inhalation device as claimed in claim 18, wherein the nozzle arrangement is designed to generate the droplet mist in the form of the spray jet, the spray jet having a cross-sectional surface area intersecting the outer housing in a region of the aperture, the cross-sectional surface area occupying at least 30% of the area of the aperture, and/or the nozzle arrangement is designed to generate the droplet mist in the form of the spray jet having an angle of opening less than 30°.

20. The inhalation device as claimed in claim 1, wherein the main axis of extent of the discharge channel encloses an angle of >0° with the dispensing direction of the nozzle arrangement, and the inhalation device comprises a liquid buffer disposed in alignment with the dispensing direction of the nozzle arrangement, the liquid buffer being configured for receiving the droplet mist if the droplet mist is not sucked into the discharge channel by respiration of the user.

21. The inhalation device as claimed in claim 20, wherein in addition to the discharge channel, an inflow channel is provided in the outer housing, the inflow channel being spaced apart from the liquid buffer and being configured such that air is sucked in through the inflow channel when the user breathes in through the discharge channel.

\* \* \* \* \*